United States Patent [19]
Ohman et al.

[11] Patent Number: 5,246,001
[45] Date of Patent: Sep. 21, 1993

[54] METHOD OF ASSESSING REPERFUSION AFTER THROMBOLYTIC THERAPY

[75] Inventors: Magnus E. Ohman, Durham, N.C.; Robert H. Christenson, Joppa, Md.; Robert M. Califf; Kristina N. Sigmon, both of Durham, N.C.

[73] Assignee: Duke University, Durham, N.C.

[21] Appl. No.: 860,856

[22] Filed: Mar. 31, 1992

[51] Int. Cl.$^5$ .............................................. A61B 5/00
[52] U.S. Cl. ................................................... 128/630
[58] Field of Search ......................... 128/630, 898, 698

[56] References Cited

PUBLICATIONS

Schoiler, V; Thode, J; Kjoller, E; "Performance characteristics of creatine kinase-MB isoenzyme measured with an immunoenzymometric and an immunoinhibition assay in acute myocardial infarction with and without thrombolytic therapy"; Jun. 1992; European Journal of Clinical Chemistry and Clinical Biochemistry; p. 357-361 Abstract.

Hohnloser, Stefan H., et al. "Assessment of Coronary Artery Patency After Thrombolytic Therapy: Accurate Prediction Utilizing the Combined Analysis of Three Noninvasive Markers", JACC vol. 18, pp. 44-99 (1991).

Christenson, Robert H., "Myocardial Injury: Diagnosis, Monitoring and Prognosis in the Thrombolytic Era" Clinical Chemistry, vol. 37, No. 6 (1991).

Christenson, Robert H., "Non-Invasive Monitoring of Thrombolysis After Mycardial Infarction", Clinical Chemistry, vol. 37, No. 6 (1991).

Christenson, Robert H., et al. "Release of the Tissue Specific MM-3 and MB-2 Isoforms of Creatine Kinase is Simultaneous During Reperfusion after Myocardial Infarction", Circulation 1990; 82 (Suppl. III) III-297.

Ohman, E. Magnus, et al., "Non-Invasive Detection of Reperfusion after Thrombolysis Using Rapid CK-MB Analysis", Circulation 1990; 82 (Suppl. III) III-281.

Creatine Kinase Isoenzymes, Edited by H. Lang, Springer-Verlag, 1981, Chapter 1.

Primary Examiner—Lee S. Cohen
Assistant Examiner—Marianne Parker
Attorney, Agent, or Firm—Bell, Seltzer, Park & Gibson

[57] ABSTRACT

The present invention is a method of diagnosing the presence of a persistent occlusion in a myocardial infarct patient undergoing thrombolytic therapy. The method comprises detecting a series of three variables from the patient and then generating the probability of the presence of a persistent occlusion from those variables. The first variable comprises a serum creatine kinase MB (CK-MB) level from a patient at the onset of thrombolytic therapy. The second variable comprises a second CK-MB level in the patient at a predetermined time after the onset of thrombolytic therapy. The third variable comprises the presence or absence of chest pain a predetermined time after the onset of thrombolytic therapy. In a preferred embodiment of the present invention, the second and third variables are detected within 30 minutes of each other and within about 1 to about 3 hours after the initial variable is detected. In an alternate embodiment a fourth variable reflecting the time from onset of chest pain to the beginning of thrombolytic therapy is included in the regression model.

16 Claims, 1 Drawing Sheet

METHOD OF ASSESSING REPERFUSION AFTER THROMBOLYTIC THERAPY

FIELD OF THE INVENTION

The present invention relates to methods of determining if reperfusion has occurred after thrombolytic therapy during a myocardial infarction.

BACKGROUND OF THE INVENTION

Early and sustained coronary artery patency after thrombolytic therapy has been implicated as one of the most important predictors of short and long term survival after acute myocardial infarction. Between 20% and 40% of patients receiving thrombolytic therapy fail to recanalize the infarct-related artery during the first few hours. Rescue angioplasty and selective infusion of fibrinolytic agents have been used successfully to restore patency of the infarct-related artery. Patients with successful rescue angioplasty have been noted to have similar long-term survival as patients who reperfuse after thrombolytic therapy alone, suggesting that procedures aimed at restoring patency after thrombolytic therapy has failed are beneficial in selected patients.

Acute coronary arteriography has to date been the only reliable method to identify patients who have failed to reperfuse. In the Thrombolysis Angioplasty in Myocardial Infarction (TAMI) 5 study a strategy using acute angiography coupled with rescue angioplasty was noted to be associated with a better overall clinical outcome after thrombolysis. However, performing acute angiography on all patients with acute myocardial infarction after thrombolysis is costly and not possible in most U.S. hospitals or in the world.

The critical importance of patency of the infarct-related artery for in-hospital and long-term survival has been documented by several studies. To non-invasively identify the subset of patients who have failed to restore patency or have incomplete reperfusion after intravenous thrombolytic therapy could allow these patients to undergo rescue angioplasty or more aggressive pharmacologic approaches.

Previous studies have examined clinical markers of reperfusion. These have included the resolution of chest pain or reperfusion arrhythmias occurring after thrombolysis. Arrhythmias have not been useful in three studies as a reliable marker of reperfusion, with sensitivities ranging between 37% and 63%. Resolution of chest pain has been a better marker of reperfusion, but has clinical disadvantages as patients perception of chest pain during myocardial infarction can be hard to interpret. Nevertheless, patients who have complete resolution of chest pain during thrombolytic therapy have a highly significant association with patency of the infarct-related artery (p=0.0005) documented during acute angiography. However, resolution of chest pain after thrombolysis is insufficient as the sole marker of reperfusion as only a small proportion of patients exhibit this phenomena.

A variety of intracellular components in the myocardium has been used to assess reperfusion. These markers have included myoglobin, myosin light chains, troponin T and both the MM and MB isoenzyme of creatine kinase (CK). Newer tissue isoforms of CK-MB also holds promise as a reliable predictors of reperfusion, but are limited by relative long assay time and lack of availability in most chemistry laboratories. In general these studies have examined the time to peak on the CK-MB release curve or used methods that require prolonged assay times. Both of these factors do not allow for early and rapid triage of patients after thrombolysis to enhance the care of patients who have failed to restore patency.

SUMMARY OF THE INVENTION

The present invention is a method of diagnosing the presence of a persistent occlusion in a myocardial infarct patient undergoing thrombolytic therapy. The method comprises detecting a series of three variables from the patient and then generating the probability of the presence of a persistent occlusion from those variables. The first variable comprises a serum creatine kinase MB (CK-MB) level from a patient at the onset of thrombolytic therapy. The second variable comprises a second CK-MB level in the patient at a predetermined time after the onset of thrombolytic therapy. The third variable comprises the presence or absence of chest pain a predetermined time after the onset of thrombolytic therapy.

In another aspect of the present invention, the method further comprises the step of determining a fourth variable comprising the time from onset of myocardial infarct symptoms in said patient to the administration of thrombolytic therapy to the patient and generating the probability of the presence of a persistent occlusion from the first through fourth variables.

In an additional aspect of the present invention, the second variable and the third variable are detected within thirty minutes of one another, and the second variable and the third variable are detected from 1 to 3 hours after the onset of thrombolytic therapy. In a further aspect of the present invention the second variable and the third variable are detected concurrently one and one-half hours after the onset of thrombolytic therapy.

DETAILED DESCRIPTION OF THE PREFERRED EMBODIMENT

Figure 1:
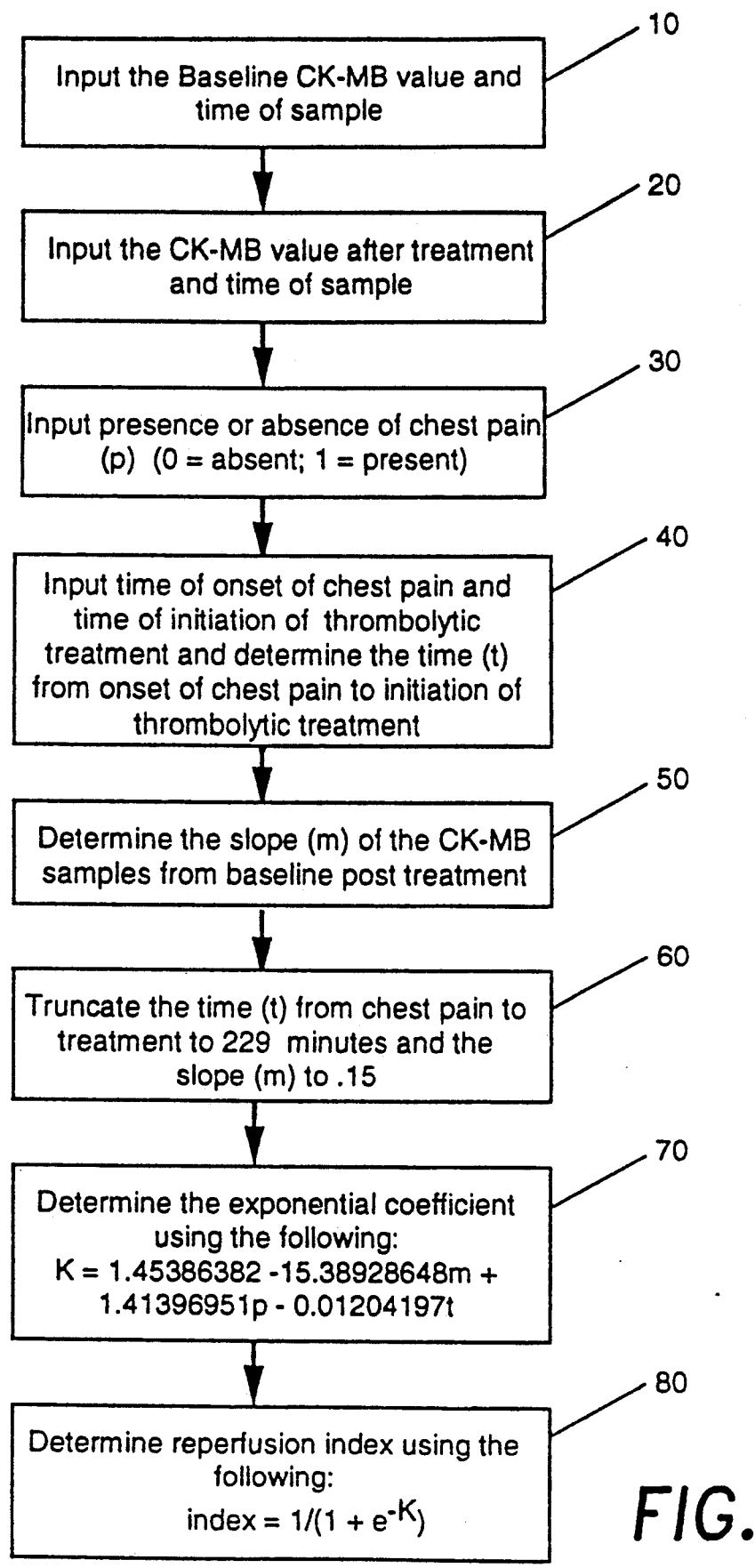
FIG. 1 is a flow diagram of the computer program which may be used to determine the reperfusion index of a patient.

The present invention is a method of determining if reperfusion occurs in a patient having a myocardial infarct and receiving thrombolytic therapy. The method of the present invention utilizes a combination of creatine kinase (CK-MB) measurements before and after thrombolytic therapy in combination with clinical information to determine the reperfusion of myocardial infarction. Measuring changes in serum CK-MB levels in conjunction with two clinical variables after starting thrombolytic therapy, can be used to identify the majority of patients who had failed to restore patency. Using such an approach it has been possible to develop a computerized model for the early noninvasive detection of reperfusion status within the first three hours of starting thrombolytic therapy, allowing early triage of such patients for acute cardiac catheterization and consideration for rescue angioplasty.

The method of the present invention involves the use of four variables in determining whether persistent occlusions are present in a patient after thrombolytic therapy. Blood samples are taken before and after thrombolytic therapy and assayed for creatine kinase MB levels.

Clinical variables of chest pain after therapy and the time from onset of chest pain to the beginning of thrombolytic therapy and the two CK-MB levels are used as inputs to a statistical model which results in the probability of the presence of a persistent occlusion.

Samples of blood are taken from the patient having already been diagnosed as having a myocardial infarction. These samples are taken prior to the beginning of thrombolytic therapy (e.g. administration of tissue plasminogen activators, streptokinase, urokinase or APSAC). The baseline sample is preferably taken with 6 hours of the onset of symptoms of the myocardial infarct (i.e. chest pain) and within 1 hour of the beginning of thrombolytic therapy. The time of sampling is recorded. The blood sample is then analyzed for serum creatine kinase MB (CK-MB) level.

After thrombolytic therapy has begun, a second blood sample is taken from the patient. This sample is take between about 1 and about 3 hours and most preferably about 90 minutes after commencing thrombolytic therapy and the taking of the baseline sample. This sample is also assayed for CK-MB level and the time of the sample is recorded.

Blood samples for the MB isoenzyme of creatine kinase (CK-MB) are collected from indwelling venous lines. A total of 10 ml of blood is drawn at the baseline (before thrombolytic therapy) and post-thrombolytic times. Blood samples are preferably collected in tubes containing no anticoagulant. In preparing the samples for test, serum is separated by centrifugation at 1000 g and aliquoted within 90 minutes of collection into screw-top freezer vials. Samples may be stored in $-70°$ C. until analysis. Various methods of CK-MB analysis are know, however, samples have been analyzed by two methods for CK-MB determination; a commercially available immunochemical assay based on the method of Wicks et al., Clinical Chemistry, 1982, 28:54–58, and; by a rapid two-site immunoassay (ICON QSR CK-MB; Hybritech Inc., San Diego, California) based on a dual monoclonal antibody technique, Piran et al., Clinical Chemistry, 1987, 33:1517–1520. The correlation between the two assays was excellent; $r=0.99$ (ICON$=1.89\times$Roche$+13$ ng/ml; Sy/x$=12.2$ ng/ml). While both methods yield acceptable results, the commercially available mass assay (Hybritech ICON QSR) is preferred. Excellent correlation between the standard activity assay (Roche) and the mass assay exist, however, the latter allows for quick determination of serum CK-MB levels required for a diagnostic test being used during the early post thrombolysis phase, where minimizing delays are essential.

As a clinical variable in the prediction of reperfusion, the presence or absence of chest pain in the patient after the commencement of thrombolytic therapy is assessed. This assessment may be carried out as a simple binary response (i.e. yes or no) as to the presence or absence of chest pain. Well recognized clinically used scale to determine the degree of severity of chest pain may be used which rates the degree of severity on a scale from 0 to 10 with 0 representing no chest pain, 2 representing mild chest pain, 5 representing moderate chest pain and 10 represent severe, extreme chest pain. The assessment of chest pain may be carried out any time after the commencement of thrombolytic therapy, preferably from 1 to 3 hours and most preferably 90 minutes after the therapy is begun. It is not essential that the assessment of chest pain and the second blood sample described above be taken concurrently. However, it is preferable that the second sample and the assessment occur within 30 minutes of each other and most preferably concurrently.

A second clinical variable which may be used in the prediction of reperfusion is the time from onset of chest pain to the administration of thrombolytic therapy. This time may be determined by calculating the difference between the time of onset of chest pain and the time thrombolytic therapy was first begun.

Through the combination of these four variables, a prediction of the reperfusion of a myocardial infarct can be made utilizing an empirically-based regression analysis model of the occurrence of persistent occlusions in myocardial infarct patients receiving thrombolytic therapy.

Using a rapid CK-MB assay combined with clinical variables results in the identification of patients who have failed to restore patency after thrombolysis. The assay used is a commercial available assay (ICON QSR CK-MB, Hybritech Inc.) that takes 20 minutes to perform using a dual monoclonal technique. The slope of CK-MB release is the variable most closely associated with reperfusion status. By including the selected clinical variables described above to the CK-MB model the capability of non-invasive detection of persistent occlusion after thrombolysis is enhanced. This combined CK-MB and clinical model results in improved diagnostic yield. The combination of these variables results in more accurate predictions than through the use of either CK-MB assays or clinical variables alone. This model can be applied during the early phase of infarction and give results within three hours of starting thrombolytic therapy. In a preferred embodiment, a computerized model is uploaded on a computer and can be placed in the clinical chemistry laboratory or emergency room to aid in the management of patients.

As seen in FIG. 1, the block diagram of the computer program of the computerized model illustrates the use of the method of the present invention.

Blocks 10 and 20, represent the collection of data from the blood samples described above. As seen in block 10, the time and level of the CK-MB baseline sample is input and stored by the computer. This baseline sample represents the pre-therapy blood sample described above. Next, as seen in block 20, the time and level of CK-MB after therapy is input and stored. This second CK-MB level is taken between 1 and 3 hours after beginning thrombolytic therapy and corresponds to the second sample described above.

Blocks 30 and 40 represent the input of clinical variables regarding the patient. As seen in block 30, the presence or absence of chest pain is input. In an alternate embodiment, the degree of chest pain could be input in place of the presence or absence of chest pain. Block 40 shows the input of the second clinical variable. From the time of onset of chest pain and the time at which thrombolytic therapy began, the time from onset of chest pain to the initiation of thrombolytic therapy is determined. The time (in minutes) from onset of chest pain to the initiation of therapy (t) is determined using the following equation:

$$t = t_4 - t_3$$

where $t_3$ is the time of onset of chest pain, and $t_4$ is the time of initiation of thrombolytic therapy. These values are input and stored for use in the predictive model as described below.

Blocks 50, 60, 70, and 80 represent the predictive determination of the persistence of the occlusion of the myocardial infarct patient. As seen in block 50, the slope of the line defined by the baseline and the post-therapy CK-MB assays is determined. The slope is calculated from the CK-MB assays using the following equation:

$$m = \frac{(L_1 - L_2)}{(t_1 - t_2)}$$

where
$L_1$ = CK-MB baseline level
$L_2$ = CK-MB post-therapy level
$t_1$ = time of baseline sample
$t_2$ = time of post-therapy sample In block 60 truncation of the slope (m) and the time from onset of chest pain to the beginning of therapy (t) are truncated to simplify the mathematical computations. The slope (m) is truncated to 0.15 if the value of m is greater than 0.15. The time (t) is truncated to 229 minutes if the value of t is greater than 229 minutes.

Block 70 illustrates the calculation of the exponential coefficient of the model of reperfusion. The following linear combination of weighted variables is used:

$$K = C + A_1 m + A_2 p + A_3 t$$

where C is a constant (C=1.45386382), m is the CK-MB slope, p is the chest pain clinical variable, t is the time from onset of chest pain to beginning of therapy and $A_1$ through $A_3$ are the following weights:
$A_1$ = −15.38928648;
$A_2$ = 1.41396951; and
$A_3$ = −0.01204197.

Preferably each of the above variables and weights are used in determining the exponential coefficient K, however, an alternate embodiment of the present invention uses only CK-MB slope and clinical chest pain information in prediction reperfusion. In this alternate embodiment, $A_3$ may be set to zero or the value of t may be set to zero. The weight $A_2$ reflects the weighting of the chest pain variable p for a binary presence or absence of chest pain. As will be understood by one of skill in the art, the value of $A_2$ may be modified using the methods described below to reflect the use of a scaled input for degree of chest pain. Utilizing the standard statistical analysis of the empirical database described below, a new weight may be obtained.

Having determined the exponential coefficient, block 80 illustrates the determination of the reperfusion index which is the probability of reperfusion. The reperfusion index is calculated using the following equation:

$$index = (1 + e^{-K})^{-1}$$

where K is the exponential coefficient described above. This combined regression model of CK-MB slope and clinical variables generates the reperfusion index or probabilities of detection of a persistent occluded infarct-related artery or incomplete reperfusion after thrombolysis. Rather than describing a predefined cut-off value to be used by physicians for an individual patient, this model could be used with different levels of "aggressive" care. The implications of such an approach are shown in Table 1. Using this approach a decision to perform acute angiography with possible rescue angioplasty could be based on the combination of clinical data and changes in serum CK-MB, giving a probability of finding an occluded infarct-related artery or suboptimal reperfusion if the patient had acute cardiac catheterization. For example, in a young patient where long term survival may be critical, a low probability (0.1) could be used to decide a triage to acute cardiac catheterization. This would lead to the majority (62%) of such patients having angiography and only a small proportion (4%) of patients with closed infarct-related artery would be missed. For an elderly patient, a different level of probability may be used to assess reperfusion status. In such a patient, one may chose a probability of 0.3 to intervene. In this scenario, 63% of patients who failed to reperfuse would be identified, while only 31% of all treated patients would undergo cardiac catheterization. This approach could potentially lead to a 13% higher early patency rate compared with a conservative approach. As described below and for uniformity, the determination of whether reperfusion has occured is based on the grade of flow following thrombolytic therapy. The flow of the infarct-related artery was graded according to the Thrombolysis in Myocardial Infarction (TIMI) Classification. The TIMI Study Group, New England Journal of Medicine, 1985, 312:932-936.

TABLE 1

Clinical Implications of a Combined Model of CK-MB Slope and Clinical Variables for Noninvasive Detection of Reperfusion Status
Persistent Occlusion
(TIMI Grade Flow 0-1)

| Probability | Sensitivity | Specificity | Cardiac Cath** | Patency With Rescue PTCA* |
|---|---|---|---|---|
| 0.80 | 4% | 99% | 2% | 76% |
| 0.50 | 42% | 92% | 16% | 84% |
| 0.30 | 63% | 79% | 31% | 88% |
| 0.20 | 88% | 70% | 44% | 93% |
| 0.10 | 96% | 49% | 62% | 95% |

Patency (TIMI Grade Flow 2 and 3)
*Patency with Rescue PTCA reflects to total patency achieved from both rescue PTCA which was applied to the patients that were identified as closed based on the predictive value in addition to those from thrombolysis alone (75%). These values are based on an 85% success rate with rescue PTCA.
**Cardiac Cath reflects the proportion of patients that would have been cathed based on the level of probability of persistent occlusion.

Recent studies have suggested that the attainment of TAMI grade 2 flow after thrombolysis may be insufficient in order to obtain myocardial salvage after thrombolytic therapy. The rapid assessment of changes in CK-MB levels after thrombolytic therapy has similar diagnostic yield when patients with TIMI grade 0 to 2 flow are compared with patients with complete reperfusion (TIMI grade 3 flow). Thus, the above regression model can be used in the method of the present invention so that the majority (85%) of patients who had not had complete reperfusion can be identified.

The weighting factors of the above equations were determined using statistical analysis of an empirical database of actual patient experience. These values may be obtained through the use of readily available statistical analysis packages for personal computers such as those offered by SAS Institute of Cary, North Carolina. Other means of regression analysis will be apparent to one of skill in the art. See generally Snedecor et al., Statistical Methods, Seventh Edition, The Iowa State University Press, 1980. Continuous variables were summarized using median and interquartile range (25th and 75th percentile) unless otherwise stated. Discrete variables were described as percentages. The difference between groups were examined using Wilcoxon rank sum test. Changes in CK-MB levels between post-therapy samples and baseline samples were examined by the difference (Delta; Pre-IRA value minus baseline value), the slope (Delta divided by the time between the samples), and the ratio (Pre-IRA value divided by baseline value). Statistical comparisons of clinical variables and CK-MB changes and the patency status (outcome) were performed using logistic regression with spline transformation. See Lee et al., American Journal of Medicine, 1986, 80:553–560. The following strategy was used to find clinical variables that might be used to augment the enzymatic prediction of patency status. Multiple linear regression was used to evaluate the relationship of clinical variables to perfusion status at acute angiography were evaluated. The candidate variables included gender, age, race, weight, time to thrombolytic therapy after onset of symptoms, infarct location, and chest pain (scale 0–10) prior to acute angiography. A similar model was then developed in the present cohort. By comparing the two models a final decision about clinically and statistically meaningful variables was then made. The best clinical variables and the optimal change in serum CK-MB was then combined to yield and overall model. This final combined model was used to generate actual probabilities based on the data entered into the combined serum CK-MB and clinical model.

To further examine the changes in CK-MB levels occurring after reperfusion, patients who had both a baseline sample and a Pre-IRA sample (n:100) were analyzed. The slope of CK-MB release (ng/ml/min) and ratio best identifies patients with either persistent occlusion (TIMI flow 0–1; Chi-square=12.5, $p=0.0049$) or incomplete reperfusion (TIMI flow 0–2; Ci-square=15.4, $p=0.0015$) of the infarct-related artery. As CK-MB slope is not dependent on exact timing of samples, it is the method used for further analysis.

The above statistical analysis can be repeated incorporating additional data from current patient information into the empirical database. The empirically-based regression analysis described above may be augmented by additional empirical data from the current patient. By including the current patient in the empirical database, the weighting factors may be updated to reflect the additional data in the computerized regression model.

The foregoing is illustrative of the present invention, and are not to be construed as limiting thereof. The invention is defined by the following claims, with equivalents of the claims to be included therein.

That which is claimed is:

1. A method of diagnosing the presence of a persistent occlusion in a myocardial infarct patient undergoing thrombolytic therapy, comprising:
   (a) detecting a first variable comprising a first serum creatine kinase MB (CK-MB) level in said patient at an onset of thrombolytic therapy; then
   (b) detecting a second variable comprising a second CK-MB level in said patient a predetermined time after the onset of thrombolytic therapy; and
   (c) detecting a third variable comprising a presence or absence of chest pain a predetermined time after the onset of thrombolytic therapy;
   (d) generating a probability of a persistent occlusion from said first through third variables.

2. A method according to claim 1, wherein said second variable and said third variable are detected within thirty minutes of one another, and wherein said second variable and said third variable are detected from 1 to 3 hours after the onset of thrombolytic therapy.

3. A method according to claim 1, wherein said second variable and said third variable are detected concurrently one and one-half hours after the onset of thrombolytic therapy.

4. A method according to claim 1, further comprising the step of:
   determining a fourth variable comprising a time elapsed from onset of myocardial infarct symptoms in said patient to an administration of thrombolytic therapy to said patient;
   and wherein said generating step comprises generating the probability of the presence of a persistent occlusion from said first through fourth variables.

5. A method according to claim 1 wherein said generating step is carried out with an empirically-based model derived from an analysis of clinical variables and creatine kinase MB enzyme levels of previous patients and the presence of reperfusion in said previous patients.

6. A method according to claim 5, further comprising the step of updating said empirically-based model to include clinical variables, creatine kinase MB enzyme levels and a presence of reperfusion of said myocardial infarct patient.

7. A method according to claim 5, wherein said empirically-based model is a regression model.

8. A method according to claim 1, wherein said first variable is detected within about 6 hours from the onset of symptoms in the patient and within about 1 hour of the onset of thrombolytic therapy.

9. A method of diagnosing the presence of a persistent occlusion in a myocardial infarct patient undergoing thrombolytic therapy, comprising:
   (a) detecting a first variable comprising a first serum creatine kinase MB (CK-MB) level in said patient at an onset of thrombolytic therapy; then
   (b) detecting a second variable comprising a second CK-MB level in said patient a predetermined time after the onset of thrombolytic therapy; and
   (c) detecting a third variable comprising a degree of chest pain a predetermined time after the onset of thrombolytic therapy;
   (d) generating a probability of a persistent occlusion from said first through third variables.

10. A method according to claim 9, wherein said second variable and said third variable are detected within thirty minutes of one another, and wherein said second variable and said third variable are detected from 1 to 3 hours after the onset of thrombolytic therapy.

11. A method according to claim 9, wherein said second variable and said third variable are detected concurrently one and one-half hours after the onset of thrombolytic therapy.

12. A method according to claim 9, further comprising the step of:
   determining a fourth variable comprising time elapsed from onset of myocardial infarct symptoms in said patient to an administration of thrombolytic therapy to said patient;
   and wherein said generating step comprises generating the probability of the presence of a persistent occlusion from said first through fourth variables.

13. A method according to claim 9 wherein said generating step is carried out with an empirically-based model derived from an analysis of clinical variables and creatine kinase MB enzyme levels of previous patients and the presence of reperfusion in said previous patients.

14. A method according to claim 13, further comprising the step of updating said empirically-based model to include clinical variables, creatine kinase MB enzyme levels and a presence of reperfusion of said myocardial infarct patient.

15. A method according to claim 14, wherein said empirically-based model is a regression model.

16. A method according to claim 9, wherein said first variable is detected within about 6 hours from the onset of symptoms in the patient and within about 1 hour of the onset of thrombolytic therapy.

* * * * *